(12) United States Patent
Shelton et al.

(10) Patent No.: US 7,347,854 B2
(45) Date of Patent: Mar. 25, 2008

(54) METHOD AND APPARATUS FOR AUTOMATICALLY MODIFYING DELIVERY PROFILE OF DRUG DELIVERY SYSTEM

(75) Inventors: Brian M. Shelton, Northridge, CA (US); Ronald J. Lebel, Sherman Oaks, CA (US); Danial H. Villegas, Granada Hills, CA (US)

(73) Assignee: Infusion Systems, LLC, Sylmar, CA (US)

( * ) Notice: Subject to any disclaimer, the term of this patent is extended or adjusted under 35 U.S.C. 154(b) by 0 days.

(21) Appl. No.: 11/069,573

(22) Filed: Feb. 28, 2005

(65) Prior Publication Data

US 2005/0197649 A1 Sep. 8, 2005

Related U.S. Application Data

(60) Provisional application No. 60/549,474, filed on Mar. 2, 2004.

(51) Int. Cl.
*A61K 9/22* (2006.01)
(52) U.S. Cl. .................................. 604/891.1
(58) Field of Classification Search ............. 604/66, 604/890.1, 891.1, 503, 93.01, 65, 502, 131, 604/151, 246
See application file for complete search history.

(56) References Cited

U.S. PATENT DOCUMENTS

| | | | |
|---|---|---|---|
| 4,146,029 A | 3/1979 | Ellinwood, Jr. | |
| 4,373,527 A | 2/1983 | Fischell | |
| 4,494,950 A | 1/1985 | Fischell | |
| 4,559,037 A | 12/1985 | Franetzki et al. | |
| 5,527,307 A * | 6/1996 | Srisathapat et al. | 604/892.1 |
| 5,814,014 A | 9/1998 | Elsberry et al. | |
| 5,836,935 A | 11/1998 | Ashton et al. | |
| 6,269,340 B1 | 7/2001 | Ford et al. | |
| 6,537,268 B1 | 3/2003 | Gibson et al. | |
| 6,562,001 B2 | 5/2003 | Lebel et al. | |
| 6,571,128 B2 | 5/2003 | Lebel et al. | |
| 6,572,583 B1 | 6/2003 | Olsen et al. | |
| 6,577,899 B2 | 6/2003 | Lebel et al. | |
| 6,579,280 B1 | 6/2003 | Kovach et al. | |

(Continued)

FOREIGN PATENT DOCUMENTS

WO  WO 03/082380  * 10/2003

(Continued)

OTHER PUBLICATIONS

EPO Supp. Search Report dated Apr. 17, 2007 for EP App. No. 05724052.

*Primary Examiner*—Kevin C. Sirmons
*Assistant Examiner*—Elizabeth MacNeill
(74) *Attorney, Agent, or Firm*—Henricks, Slavin & Holmes LLP

(57) ABSTRACT

The present invention relates to an implantable drug delivery device which includes a fluid drug reservoir, a catheter, a controllable fluid transfer device, e.g., a pump or valve, and a drug delivery control means. The control means in accordance with the invention is configured to initially clear a first, or old, drug from the device based on the content of the Current Profile data containing a first, or old, delivery profile. After the old drug is cleared, then the control means automatically modifies the Current Profile data to match a second, or new, delivery profile for controlling delivery of a second, or new, drug.

24 Claims, 5 Drawing Sheets

U.S. PATENT DOCUMENTS

| | | |
|---|---|---|
| 6,585,644 B2 | 7/2003 | Lebel et al. |
| 6,605,072 B2 | 8/2003 | Struys et al. |
| 6,648,821 B2 | 11/2003 | Lebel et al. |
| 6,668,196 B1 * | 12/2003 | Villegas et al. ............... 607/60 |
| 6,687,546 B2 | 2/2004 | Lebel et al. |
| 6,740,075 B2 | 5/2004 | Lebel et al. |
| 6,810,290 B2 * | 10/2004 | Lebel et al. ................. 607/60 |
| 2001/0044620 A1 * | 11/2001 | Krulevitch et al. ...... 604/892.1 |
| 2002/0019606 A1 | 2/2002 | Lebel et al. |
| 2003/0045858 A1 | 3/2003 | Struys et al. |
| 2003/0060753 A1 | 3/2003 | Starkweather et al. |

FOREIGN PATENT DOCUMENTS

WO     WO 03/082380 A1     10/2003

* cited by examiner

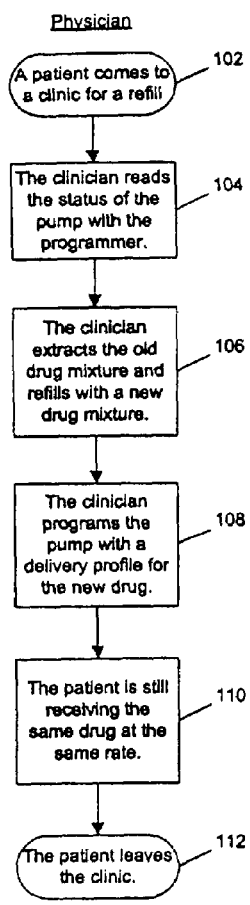
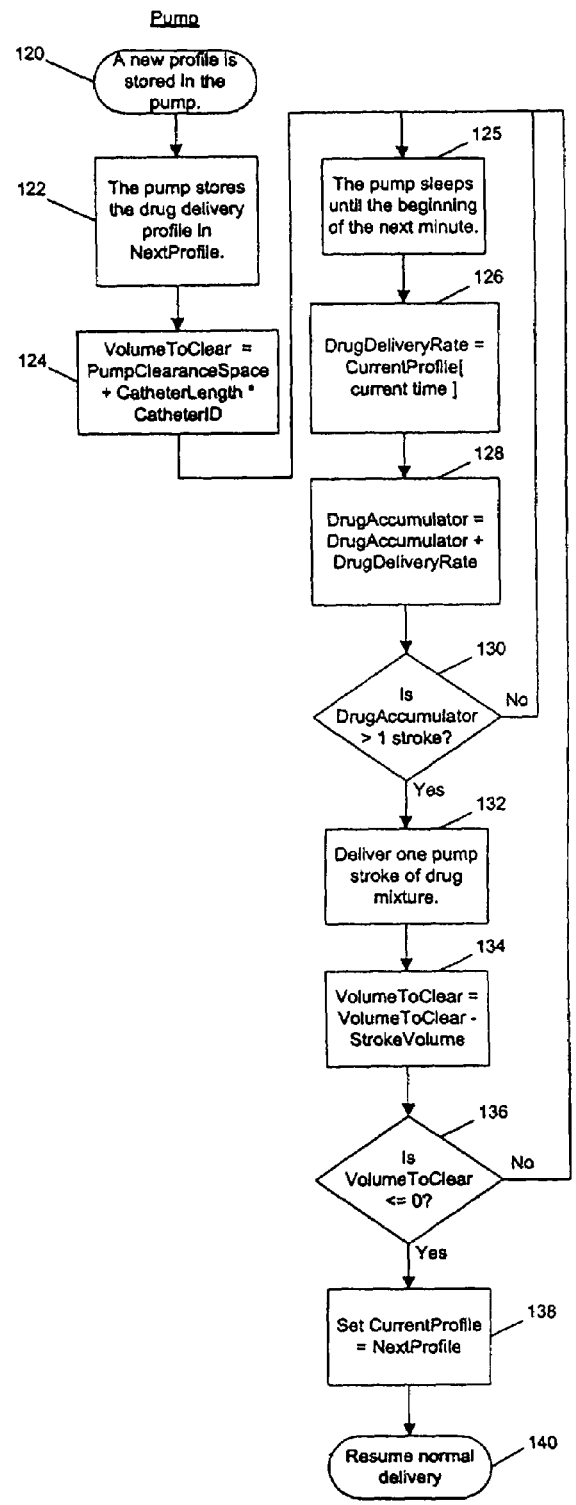
Figure 5A
Figure 5B

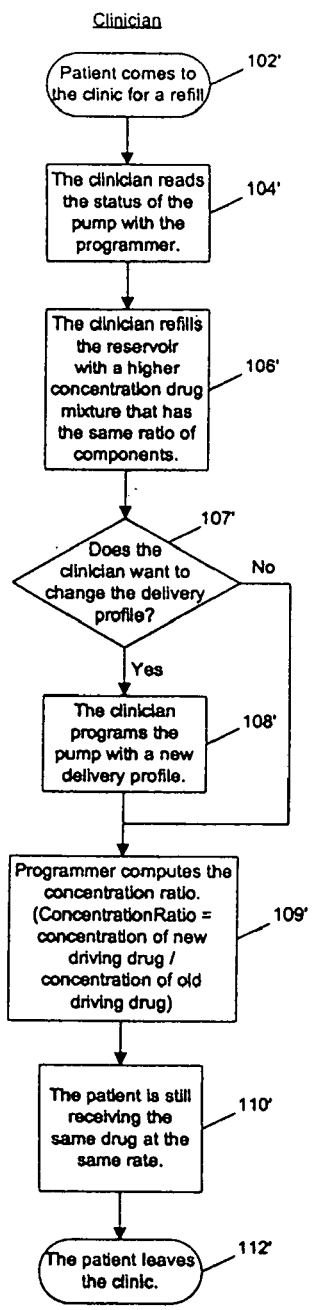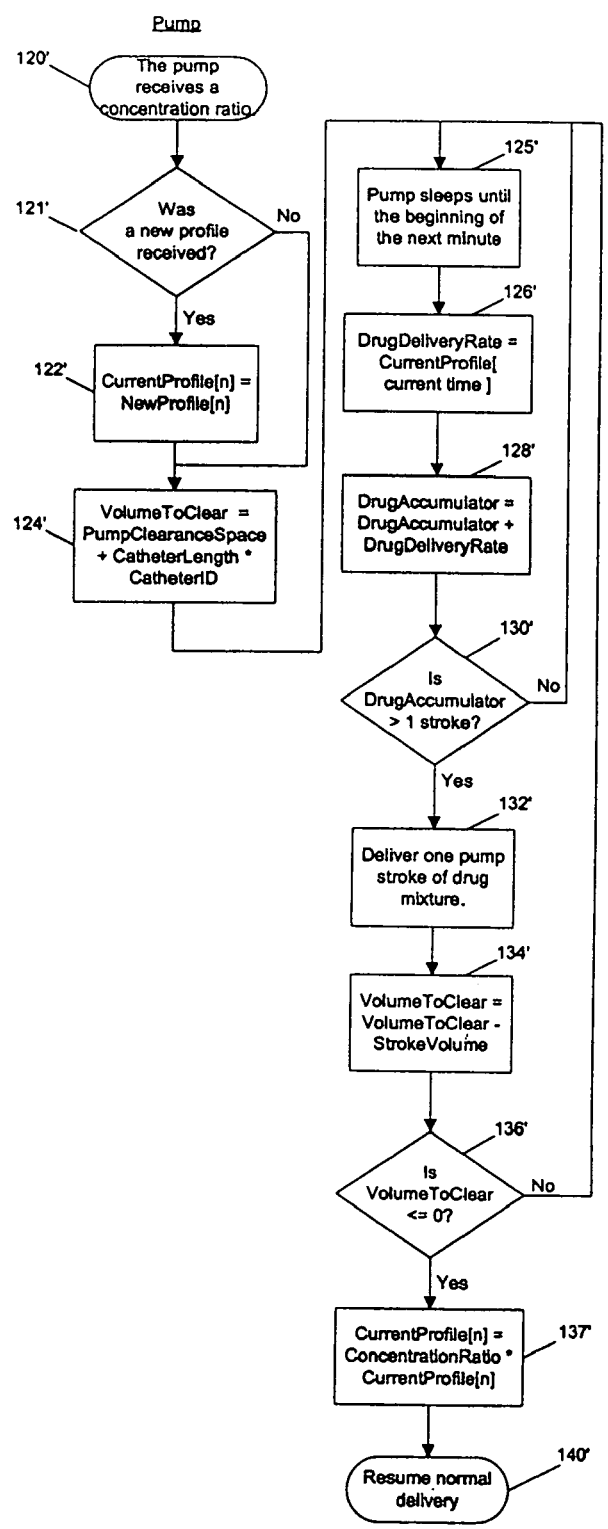
Figure 6A
Figure 6B

METHOD AND APPARATUS FOR AUTOMATICALLY MODIFYING DELIVERY PROFILE OF DRUG DELIVERY SYSTEM

RELATED INVENTION

This application claims the benefit of U.S. provisional application 60/549,474 filed 2 Mar. 2004.

FIELD OF THE INVENTION

This invention relates generally to implantable medical devices which deliver a therapeutic drug to a body site at flow rates and times specified by a drug delivery profile arid, more particularly, to such devices and methods of operation for automatically modifying a Current Profile to accommodate changes in the drug formulation being delivered.

BACKGROUND OF THE INVENTION

Various implantable drug delivery devices are known in the art which can be programmed to deliver a drug to a body site for infusion at flow rates and times dictated by a stored drug delivery profile. Such delivery devices typically include a refillable reservoir for storing a fluid drug and a controllable fluid transfer device (e.g., a pump or valve) for transferring fluid from the reservoir to a catheter for delivery to the body site. The drug delivery profile comprises a data set specifying a schedule of flow rates for a periodic cycle, or period, of a certain duration. For example, the duration of a period can be one day, one week, or one month, etc. The particular profile used to control drug delivery is typically specified by the patient's clinician and depends upon several factors including the particular drug formulation being delivered, the patients condition, the therapy being administered, etc.

Most modern drug delivery devices permit a clinician to modify a patient's drug therapy by modifying a stored delivery profile, and/or replacing the current, or old, drug with a new drug. As used herein, the term "new" drug refers to a change in formulation and is intended to include a change in concentration and/or a change in active components. Regardless, if an old drug is replaced by a new drug, then a Current Profile must also be changed to assure that the new drug is properly delivered with regard to safety and efficacy.

Modern implantable drug delivery devices generally permit a clinician to evacuate the volume of old drug from the reservoir prior to introducing a new drug. Although the reservoir can be evacuated, a certain amount of old drug generally remains in the system, typically in the pump (i.e., pump clearance space) and catheter (i.e., catheter clearance space). Any old drug remaining in the system is typically cleared by delivery to the patient's body site. Although, it is generally desired to clear the old drug rapidly in order to promptly initiate the new therapy, the delivery rate must not be so rapid as to jeopardize the patient's health or safety. In any event, the delivery profile for the old drug is generally different than the profile for the new drug. Traditionally, the transition from an old drug to a new drug is typically handled by the clinician calculating a "bridge bolus" to rapidly clear the old drug. Calculation of this bridge bolus and the associated bolus rate is generally time consuming for the clinician and represents an opportunity for human error.

SUMMARY OF THE INVENTION

The present invention relates to an implantable drug delivery device which includes a fluid drug reservoir, a catheter, a controllable fluid transfer device, e.g., a pump or valve, and a drug delivery control means. The control means in accordance with the invention is configured to initially clear a first, or old, drug from the device based on the content of the Current Profile data containing a first, or old, delivery profile. After the old drug is cleared, then the control means automatically modifies the Current Profile data to match a second, or new, delivery profile for controlling delivery of a second, or new, drug.

In accordance with a preferred embodiment of the invention, the drug delivery control means comprises a controller, e.g., a microprocessor or microcontroller, programmed to defer adoption of a new delivery profile, as the Current Profile, until a remaining, or "clearance", volume of the old drug has been cleared from the device. More particularly, the controller, upon receipt of a new profile, determines the Clearance Volume, i.e., the volume of the old drug which remains to be cleared. The controller then monitors the subsequent delivery of the old drug to the patient to determine when the remaining old drug has been cleared from the device. Thereafter, the controller adopts the new profile as the Current Profile.

In accordance with the preferred embodiment, after a new drug has been introduced into the reservoir and a new profile has been loaded into the controller, the controller retains the new profile in a Next Profile storage location. The contents of the Next Profile storage location is then used as the Current Profile data after the old drug has been cleared from the device.

In accordance with a significant aspect of the invention, the quantity of remaining old drug delivered subsequent to receipt of a new delivery profile is preferably determined by monitoring the activity of the fluid transfer device. This technique assures that any delivery of the old drug, whether attributable to the old delivery profile and/or a bolus administered by a clinician or the patient, will be taken into account.

BRIEF DESCRIPTION OF THE FIGURES

FIGS. 5A and 5B are flow charts respectively depicting the activity of the clinician in changing the drug being administered and the algorithm executed by the implanted controller to automatically switch the Current Profile from a first delivery profile to a second delivery profile; and FIGS. 6A and 6B are similar to FIGS. 5A and 5B for the special case where the first and second drugs differ in concentration only.

DETAILED DESCRIPTION

Figure 1:
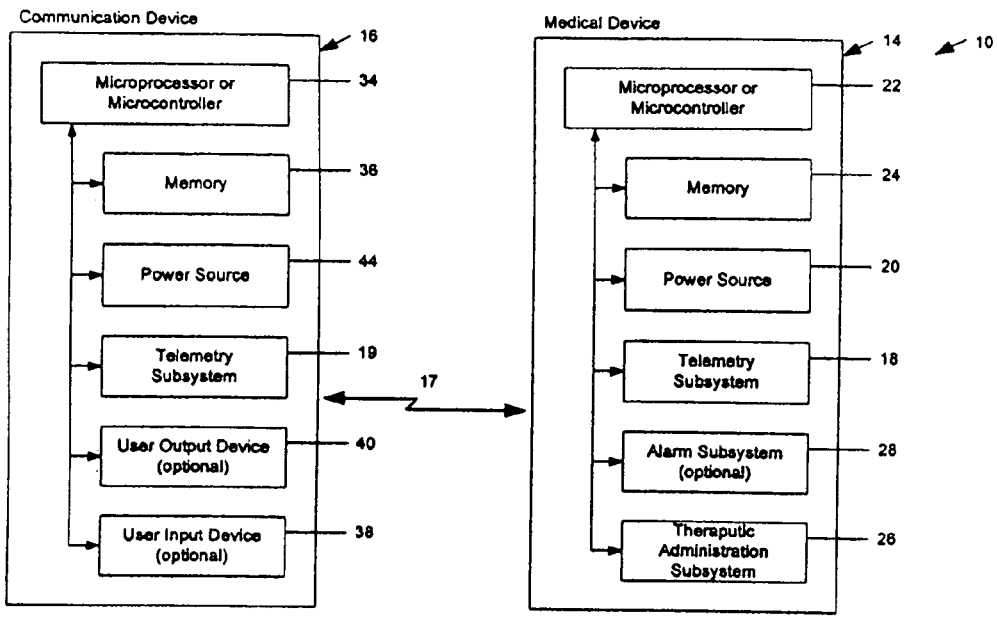
FIG. 1 is a block diagram of an exemplary medical system comprised of an implantable medical device, e.g., a drug delivery device, and an external communication device, or programmer.

Attention is initially directed to FIG. 1 which presents a generalized block diagram of a medical system 10 comprised of at least one medical device (MD) 14, e.g., an implantable drug delivery device, or pump, and an external communication or programmer device (CD) 16. The system of FIG. 1 is configured to enable the medical device 14 and the communication device 16 to communicate, e.g., via RF telemetry 17, using MD telemetry subsystem 18 and CD telemetry subsystem 19, respectively contained within the devices 14 and 16. The medical device 14 will be assumed to be implanted in a patient's body for the purpose of performing a therapeutic function, such as controlled drug delivery. The communication device 16, on the other hand, is intended to be deployed external to the body and available for use by a physician or clinician or patient to transmit control and/or data signals to the device 14. For example, using the communication device 16, a clinician is able to produce signals which are transmitted via RF link 17 to the medical device 14 to affect its therapeutic performance such as by modifying its drug delivery profile. Systems of the type depicted in FIG. 1, as thus far described are well known. The present invention is directed to a method and apparatus particularly configured to automatically coordinate a change in the drug currently being delivered with a modification of the drug delivery profile currently in use, i.e., the Current Profile.

As depicted in FIG. 1, a typical medical device 14 in system 10 includes an internal power source 20, e.g., a battery, a controller 22, e.g., a microprocessor or microcontroller, and a memory 24 associated therewith for storing programs and/or data. The controller 22 operates to execute a stored program to control therapeutic subsystem 26 to controllably deliver a drug to a patient's body site. The device 14 may also include an alarm subsystem 28 controllable by controller 22 to alert the patient or clinician of some monitored event.

Communication device 16 is shown as including a CD programmer 34, e.g., a microprocessor or microcontroller, which operates in conjunction with memory 36 which stores programs and/or data. The device 16 optionally includes a CD user input device 38, e.g., a keyboard, and a CD user output device 40, e.g., a display. The communication device 16 further includes aforementioned CD telemetry subsystem 19 configured to transmit signals to or receive signals from the MD telemetry subsystem 18. The communication device 16 further includes an internal power source 44 which can comprise a battery or any other suitable conventional power source.

In a typical system 10, the communication device 16 is capable of sending messages to the medical device 14 for use by its controller 22 to affect the operation of its therapeutic administration subsystem 26. Additionally, the medical device 14 is typically capable of sending messages to the communication device 16 to report various conditions, e.g., battery status, drug reservoir status, etc. These respective messages sent by the communication device 16 and medical device 14 are handled by the respective telemetry subsystems 19 and 18, each of which is able to transmit and receive RF telemetry signals. Typically, these RF telemetry signals comprise bit streams carried by an RF carrier signal of specified frequency.

Figure 2:
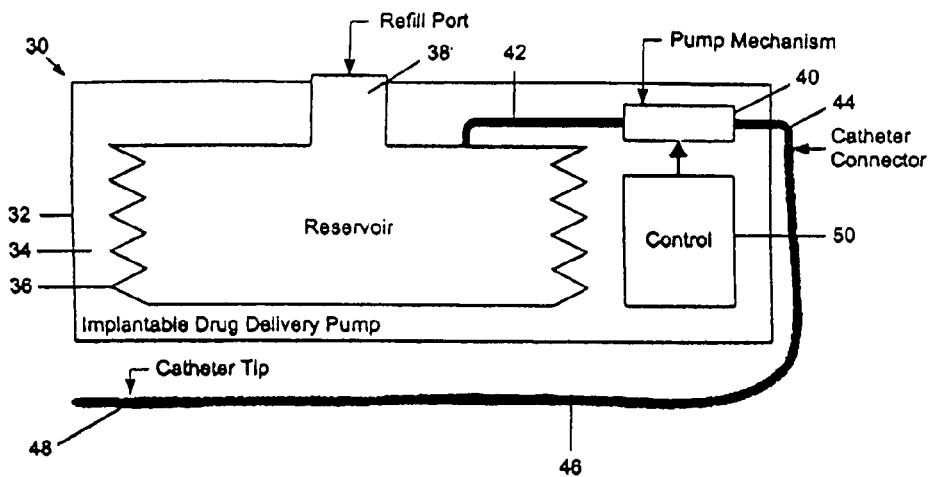
FIG. 2 is a schematic diagram of an exemplary implantable drug delivery device.

FIG. 2 illustrates a typical implantable drug delivery device 30 comprising a sealed housing 32 defining an interior volume 34. A reservoir 36 for storing the drug to be delivered is mounted in the housing 32 and has an inlet coupled to a fill port 38. A controllable fluid transfer device 40, e.g., a pump or valve mechanism, couples a reservoir outlet via tube 42 to the proximal end 44 of a catheter 46. The catheter distal end 48 is intended to be implanted proximate to a target site in the patient's body for delivering the drug thereto. FIG. 2 also shows a controller 50 for controlling the fluid transfer device 40. Controller 50 corresponds to controller 22 and associated elements shown in device 14 in FIG. 1.

In typical use, a hypodermic needle (not shown) is used, via fill port 38, to fill the reservoir 36 with a first drug. The fluid transfer device 40 is controlled by controller 50 in accordance with Current Profile data, containing data appropriate to the first drug, drug delivery profile to deliver the drug to the catheter proximal end. The drug delivery profile data which specifies a schedule of drug flow rates over a certain period, or cycle, e.g., having a duration of one day or one week or one month.

Figure 3A:
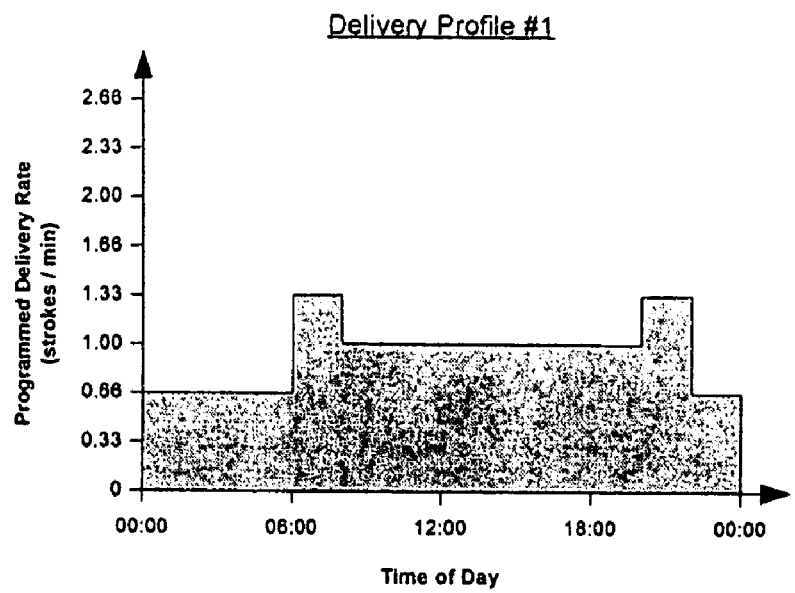
FIGS. 3A and 3B respectively represent exemplary first and second drug delivery profiles for controlling an implanted fluid transfer device, e.g., a pump, to deliver first and second drugs.
Figure 3B:
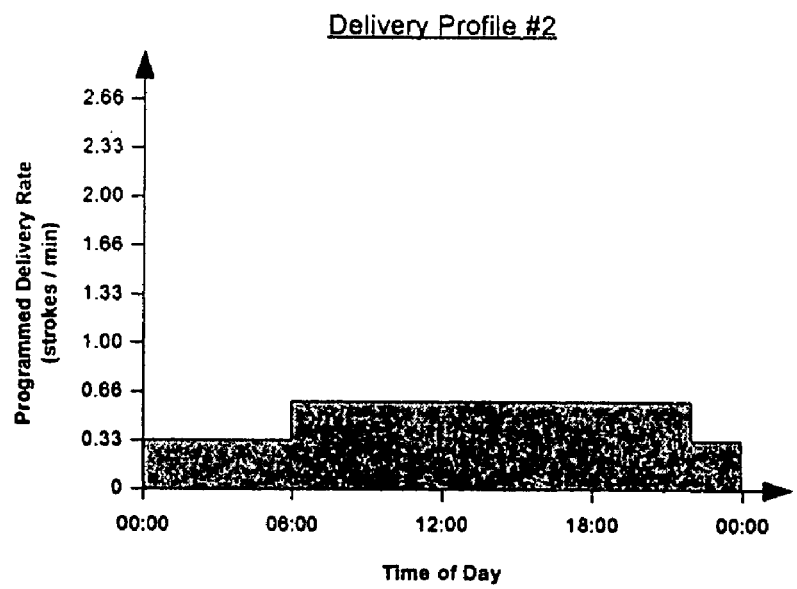

FIGS. 3A and 3B respectively represent exemplary first and second drug delivery profiles 54 and 56 appropriate for delivering exemplary first and second drugs, respectively. The exemplary profiles 54 and 56 represent drug delivery schedules for a period of certain duration, i.e., a 24 hour duration. Exemplary profile 54, for example, specifies that from 00:00 to 06:00 hours, a first drug is to be delivered at a rate of 0.66 strokes/minute, from 06:00 to 08:00 at a rate of 1.33 strokes/minute, from 08:00 to 20:00 at a rate of 1.0 strokes/minute, from 20:00 to 22:00 at a rate of 1.33 strokes/minute, and from 22:00 to 24:00 at a rate of 0.66 strokes/minute. The exemplary drug delivery profiles 54, 56 represented in FIGS. 3A and 3B are typically specified by the patient's clinician via programmer 16 to achieve the desired therapy. The drug delivery profiles specified by the programmer 16 are typically converted by the controller 50 into an equivalent operational schedule for the fluid transfer device 40, e.g., strokes per minute, to achieve the desired drug delivery flow rates.

Figure 4:
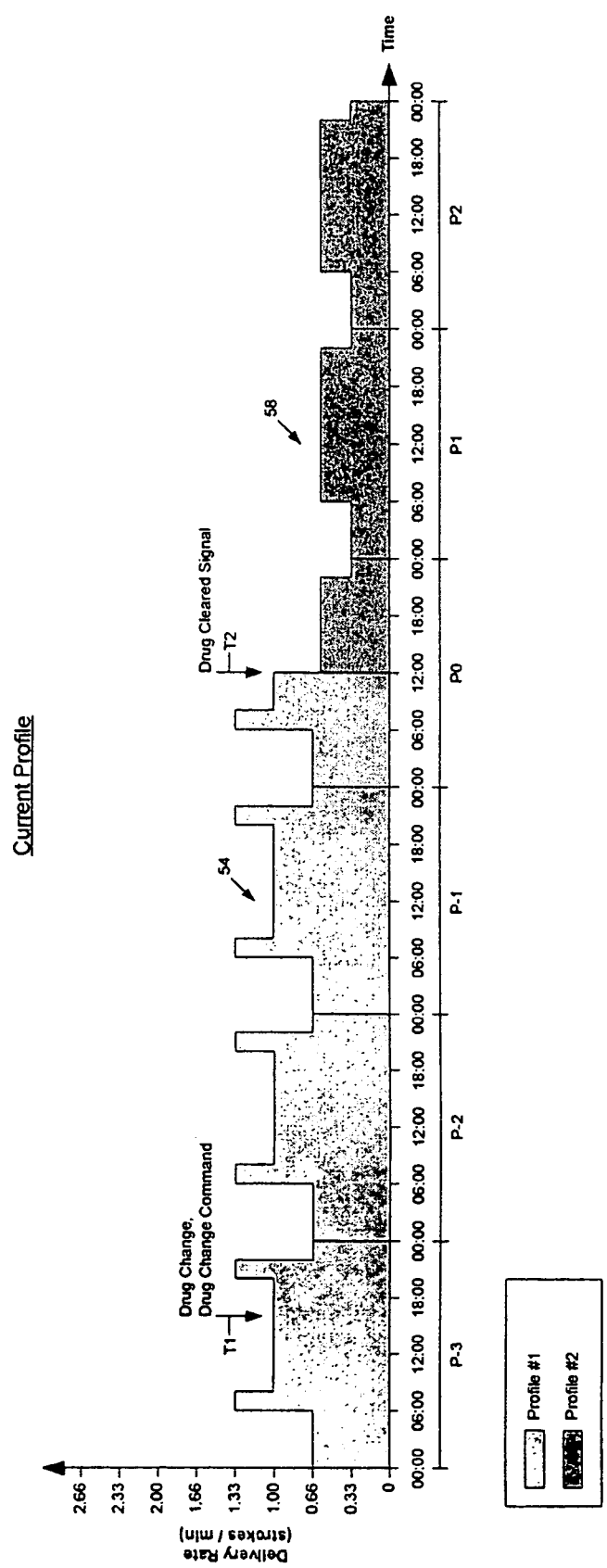
FIG. 4 is a time chart depicting the manner of switching from a first delivery profile to a second delivery profile after a first drug is cleared from the implanted device.

Attention is now directed to FIG. 4 which comprises a timing chart generally depicting the manner of transitioning the Current Profile data from the first to the second delivery profile in order to accommodate a change in drug formulation. More particularly, note in FIG. 4 that for periods P-3, P-2, P-1, the Current Profile uses the first delivery profile 54 for delivering the first drug. Now assume that at time T1, the clinician chooses to modify the therapy and accordingly evacuates the first drug from the reservoir and then refills the reservoir with the second drug. This action is accompanied by the clinician, i.e., programmer 14, issuing a drug change command.

In accordance with the present invention, as represented in FIG. 4, the Current Profile will continue to use the first delivery profile 54 until the first drug remaining in the pump and catheter clearance spaces is cleared from the device. When this occurs, a drug cleared signal is generated at time T2 causing the second delivery profile 56 to thereafter be used as the Current Profile.

Attention is now directed to FIG. 5A which, in flow chart form, depicts a typical sequence of actions occurring when a patient having an implanted drug delivery device visits a clinic. In a typical situation as represented by block 102, the patient will periodically visit the clinic in order to have his implanted reservoir refilled. As represented by block 104, the clinician will read the status of the drug delivery device, typically via the external communication device, or programmer 16 (FIG. 1). The clinician may determine that a new drug therapy should be initiated which may involve the utilization of a new, or second, drug to replace of the old, or first, drug presently in the reservoir. The term "new drug" as used herein is intended to cover any change in the drug formulation including changes in active components or merely changes in concentration. If the clinician determines that a new drug is appropriate, then, as represented by block 106, he will extract the old drug from the reservoir and refill the reservoir with the new drug. The clinician will also program the drug delivery device (block 108) utilizing the external programmer 16 which action will generate the drug change command shown at time T1 in FIG. 4. In accordance with the present invention, the drug delivery device will continue to deliver the first, or old, drug to the patient in accordance with the Current Profile data defined by the old delivery profile (block 110) until the old drug is cleared from the delivery device (at time T2 in FIG. 4). The patient may then leave the clinic (block 112). Thereafter, the implanted drug delivery device in accordance with the present invention will automatically switch to the new drug profile once all of the remaining old drug has been cleared from the delivery device.

FIG. 5B illustrates a flow chart which depicts a program executable by the drug delivery device microprocessor 22 for clearing a first, or old, drug from the device in accordance with a first, or old, delivery profile and then after the first drug has been cleared, automatically adopting a second, or new, profile for delivery of a second, or new, drug introduced by the clinician into the device reservoir.

The flow chart of FIG. 5B in initial block 120 shows that a second, or new, delivery profile is stored in the drug delivery device, typically as a consequence of clinician use of the external programmer which generates the drug change command (FIG. 4). The delivery device temporarily stores the new drug delivery profile in a NextProfile register, or storage location, (block 122). FIG. 5B assumes that when the new profile is stored in the drug delivery device, the clinician contemporaneously extracts, or evacuates, the old drug from the delivery device reservoir. It should be understood that the evacuation of the old drug from the reservoir does not fully evacuate the old from the delivery device. Rather, some of the old drug remains in the delivery device clearance space, i.e., within the pump and the catheter. The delivery device microprocessor 22 is able to determine the quantity of old drug remaining to be cleared as a consequence of previously stored data defining the pump clearance space, the catheter length, and the catheter inner diameter. More particularly, the volume of the pump clearance space is known at the time of manufacture and can be programmed into the microprocessor 22 at that time. The volume of the catheter clearance space has to be programmed into the microprocessor at the time of, or subsequent to implant after the final catheter dimensions are known. Once the physician has programmed the catheter information into the pump, a "profile bridge" can be performed for each drug change, drug concentration change, or drug mixture reformulation. The "profile bridge" is the pump's continuation of basal delivery using the old basal profile until it has delivered all of the old drug or drug mixture. The algorithm for this profile bridge is depicted in FIG. 5B which assumes that the catheter information has already been programmed into the pump.

Based on the known pump and catheter data, the microprocessor 22, in block 124, calculates the quantity of old drug which must still be cleared from the delivery device in accordance with the old delivery profile. After the remaining old drug volume to be cleared is calculated in block 124, blocks 125 and 126 are executed. Block 125 introduces a wait interval. Block 126 indicates that the current drug delivery rate of the pump is still controlled by the CurrentProfile data based on the old delivery profile. Consequently, the fluid transfer device or pump continues to deliver the old drug at the rate specified by the old profile stored in the CurrentProfile register.

Block 128 develops a DrugAccumulator value based on the delivery profile stored in the Current Profile register. Once the DrugAccumulator value is greater than one pump stroke, then decision block 130 provides a "yes" output and operation proceeds to block 132. On the other hand, if block 130 produces a "no" response, then operation loops back to block 125 which iteratively enableS the DrugAccumulator value to increase to one stroke.

Block 132 occurs when the DrugAccumulator value exceeds one stroke meaning that the fluid transfer device or pump should be actuated to deliver a unit quantity of the old drug via the catheter to the patient's body site. In block 134 a previously calculated VolumeToClear value is decremented by the volume of drug moved by the pump stroke. Decision block 136 compares the decremented VolumeToClear value with zero. If the VolumeToClear value has not yet decremented to zero, then operation loops back to block 125 to continue clearance of the old drug. On the other hand, if block 136 produces a "yes" result (meaning that the old drug has been fully cleared), then operation proceeds to block 138 which adopts the new drug delivery profile, stored in the NextProfile register in block 122, as the CurrentProfile. Then, operation continues based on the new delivery profile to cause the fluid transfer device to thereafter deliver the new drug according with the new profile, as was demonstrated in FIG. 4. FIG. 5B depicts an algorithm which is generally applicable to any type of drug formulation change. A special nontrivial type of drug formulation change frequently occurs involving a change in concentration only. In this special case, the new profile can be developed by arithmetically manipulating the old profile; e.g., multiplying the old profile by a ratio reflecting the concentration of the new drug to the concentration of the old drug.

FIG. 6A is similar to FIG. 5A but contemplates the special case where the old and new drug formulations differ solely by concentration. Note that FIG. 6A includes blocks 102' and 104' which correspond identically to blocks 102 and 104 of FIG. 5A. Block 106' differs from block 106 in that it involves the clinician refilling the reservoir with a higher concentration drug formulation having the same ratios of active components. In block 107', the clinician indicates to the programmer 16 whether he also desires to change the delivery profile. If yes, the clinician programs a new delivery profile in block 108'. Regardless, the programmer 16 then computes the concentration ratio (Concentration Ratio) representing the relative concentrations of the old and new drugs (block 109'). Blocks 110' and 112' correspond to blocks 110 and 112 of FIG. 5A.

FIG. 6B comprises a flow chart depicting the program executed by microprocessor 22 for the special case where the new and old drugs differ solely in concentration. The sequence of FIG. 6B is initiated (block 120') when the programmer 16 sends the concentration ratio (computed in block 109') to the microprocessor 22. Block 121' asks if a new delivery profile has been received from the programmer (e.g., as a consequence of block 108'). If yes, operation proceeds to 122' which replaces the CurrentProfile with the NewProfile. If no, operation skips block 122' and proceeds directly to block 124'. Block 124' corresponds to block 124 (FIG. 5B) and is followed by blocks 125', 126', 128', 130', 132', 134', and 136', all of which respectively correspond to similarly numbered blocks in FIG. 5B.

After block 136' recognizes that the old drug has been cleared, operation proceeds to block 137' which scales the CurrentProfile by the ConcentrationRatio received from the programmer (block 120'). Then normal delivery is resumed in block 140'.

From the foregoing, it should be understood that a method and apparatus has been disclosed herein for automatically bridging the delivery profiles respectively associated with a first or old drug and a second or new drug. The method and apparatus described herein relieves the clinician of the task of determining a bolus rate which is frequently time consuming and represents an opportunity for human error. An apparatus operating in accordance with the present invention operates to more smoothly bridge the delivery rates respectively associated with different first and second drugs.

It is pointed out that the term drug delivery profile has been used herein to generally refer to a set of data describing a schedule of flow rates. A drug delivery profile typically refers to a single period or cycle of certain duration, e.g., 24 hours, or one week, or one month, etc. The drug delivery profile data can be organized in any of various ways, all consistent with the teachings of the present invention. For example, the drug delivery data can be consistent with any of the following approaches or any combination thereof:

1. A single, constant drug infusion rate
2. Multiple drug infusion rates, which can be specified in the following ways:
   a. A set of start times and rates
   b. A set of start times, end times and amounts
3. A periodic bolus, which can be specified in the following ways:
   a. Amount and an interval between boluses
   b. Rate, duration, and interval between boluses
4. A repeating pattern of bolus amounts and delays till the next bolus:
   a. A set of bolus amounts and delays till the next bolus
   b. A set of bolus rates, durations, and delays until the next bolus It is, of course, recognized that a system in accordance with the invention that automatically switches delivery profiles relies on accurate VolumeToClear and DrugAccumulator data. If the mechanism cannot deliver accurately, then it might switch profiles either early or late. This, in turn, could result in an over-delivery situation. To mitigate this potential safety issue, it is sometimes prudent to intentionally deliver the drug at the slower rate during the period of uncertainty; i.e., during the period when either drug could be delivered from the tip of the catheter.

It is possible to assert that the implantable drug-delivery pump does not really need to know if the concentration of the drug increases or decreases at a refill. When the pump is done bridging, it will switch from one basal-rate profile to another. If only a single basal rate were delivered for each profile, then the pump could switch from a high rate to a low rate earlier than from a low rate to a high rate. This would avoid the delivery of a high concentration drug at a high rate. This idea can be extended to a basal-rate profile with multiple basal rates by averaging the rates across the entire profile duration. In the case of a daily profile, this would be the total amount of drug that is delivered in twenty four hours. If the daily delivery rate decreases with a refill, the pump should begin using the new profile after the minimum clearance volume has been delivered.

Another solution to the problem of selecting the minimum or maximum bridge volume is to simply have the clinician specify which to use. Bridging in this manner is performed by tracking the amount of drug that has been delivered after a drug change. Therefore, it accounts for both basal and bolus delivery. However, if the rates, duration, or limits to patient-requested boluses are changed by the clinician, these changes should take effect at the end of the bridging period (i.e., when the new drug is being delivered from the tip of the catheter).

The programmer is preferably configured to also allow the clinician to specify the type of procedure (e.g., refill, drug formulation change, or drug concentration change). The programmer will then signal the implanted pump to start a bridging operation. If a simple drug concentration change is performed, the programmer will compute the ratio between the two drugs and then send this information to the pump. In this manner, the bridging would be programmed by the clinician specifying the type of operation rather than explicitly specifying that a bridge is desired.

The invention claimed is:

1. A method of operating an implantable drug delivery that includes a reservoir, a fluid transfer device, and a catheter, said method comprising the steps of:
   filling said reservoir with a first drug;
   controllably transferring said first drug from said reservoir to said catheter and a body site in accordance with a first delivery profile specifying a schedule of at least two different flow rates during a delivery period of certain duration;
   evacuating said first drug from said reservoir;
   filling said reservoir with a second drug;
   providing a second delivery profile specifying a schedule of flow rates for transferring said second drug to said catheter;
   determining the quantity of first drug remaining by monitoring activity of the fluid transfer device, and continuing to transfer the remaining quantity of said first drug in said delivery device to said body site in accordance with said first delivery profile, after evacuating said reservoir; and
   initiating controllable transfer of said second drug from said reservoir to said catheter in accordance with said second delivery profile after said remaining quantity of said first drug has been cleared from said device in accordance with the first delivery profile.

2. The method of claim 1 wherein said step of controllably transferring said first drug from said reservoir includes the step of:
   operating a programmable microprocessor to control a controllable fluid transfer device.

3. The method of claim 1 wherein said step of determining the quantity of first drug remaining includes the step of calculating the difference between a stored quantity of said first drug and a quantity of drug transferred from said delivery device after evacuation of said reservoir.

4. The method of claim 1, wherein the delivery period of certain duration comprises a twenty-four hour period.

5. The method of claim 1, wherein the step of determining the quantity of first drug remaining by monitoring activity of the fluid transfer device comprises the step of determining the quantity of first drug remaining by monitoring pump strokes.

6. An implantable fluid delivery device comprising:
   a reservoir for storing a fluid;
   a catheter for transferring fluid from said reservoir to a selected body site, said catheter having a proximal end for receiving fluid from said reservoir and a distal end for delivering fluid to said body site;
   a controllable pump coupling said reservoir to said catheter proximal end;

a controller for storing a current delivery profile;

means for introducing a first fluid into said reservoir;

means for storing a first delivery profile, including at least two different flow rates during different intervals within a period of certain duration, in said controller as said current delivery profile for specifying a schedule of flow rates for said first fluid;

means for supplying a second delivery profile to said controller specifying a schedule of flow rates for a second fluid;

means for determining the quantity of said first fluid remaining in said delivery device by monitoring pump actuations;

said controller being operable to control said pump in accordance with said current delivery profile to deliver said first fluid to said body site at rates specified by said first delivery profile and to adopt said second delivery profile as said current delivery profile in response a determination by the means for determining that said first fluid has been fully cleared from said delivery device in accordance with the first delivery profile.

7. The delivery device of claim 6 wherein said controller comprises a programmable microprocessor.

8. The delivery device of claim 6 further including means for selectively evacuating fluid from said reservoir.

9. The delivery device of claim 6 in combination with an external programmer for supplying said second delivery profile.

10. The delivery device of claim 9 wherein said second delivery profile is applicable to a period of certain duration and specifies at least two different flow rates during different intervals within said period.

11. The delivery device of claim 6 wherein said means for determining the quantity of first fluid remaining in said delivery device includes means for calculating the difference between a quantity of fluid stored in said delivery device and a quantity of fluid transferred by said pump.

12. The delivery device of claim 6, wherein the period of certain duration comprises a twenty-four hour period.

13. An implantable drug delivery device comprising:
a reservoir for storing a fluid drug;
means for introducing a first fluid into said reservoir;
a catheter for transferring a fluid from said reservoir to a selected body site, said catheter having a proximal end for receiving fluid from said reservoir and a distal end for delivering fluid to said body site;
a controllable fluid transfer device coupling said reservoir to said catheter proximal end;
a controller for storing a current delivery profile;
means for storing a first delivery profile in said controller as said current delivery profile;
means for evacuating said first fluid from said reservoir and introducing a second fluid into said reservoir;
means for supplying a second delivery profile for a second fluid;
means for determining the quantity of said first fluid transferred from said delivery device in accordance with said first delivery profile and any bolus delivery requests subsequent to an evacuation of the first fluid from the reservoir;
means for operating said fluid transfer device in accordance with said current delivery profile to deliver said first fluid through said catheter to said body site at the schedule of flow rates specified by said first delivery profile subsequent to an evacuation of said first fluid from said reservoir; and means for adopting said second delivery profile as said current delivery profile in response to a determination by the means for determining that said first fluid being fully cleared from said delivery device.

14. The delivery device of claim 13 wherein said fluid transfer device comprises at least one pump.

15. The delivery device of claim 13 wherein said fluid transfer device comprises at least one valve.

16. The delivery device of claim 13 wherein at least one of the first and second delivery profiles defines a schedule of at least two different flow rates for a period of certain duration.

17. The delivery device of claim 13 wherein said controller includes a programmable microprocessor.

18. The delivery device of claim 13 in combination with an external programmer selectively operable to supply a delivery profile to said delivery device.

19. The delivery device of claim 16, wherein the delivery period of certain duration comprises a twenty-four hour period.

20. A method of operating an implantable drug delivery device including a reservoir, a fluid transfer device and a catheter, the method comprising the steps of:
transferring a first drug from the reservoir to the catheter in accordance with a first delivery profile;
transferring a second drug from the reservoir to the catheter in accordance with the first delivery profile and at least one bolus delivery request, after the first drug has been evacuated from the reservoir in such a manner that a quantity of the first drug remains in the fluid transfer device and/or the catheter subsequent to the evacuation and after the reservoir has been filled with a second drug, so long as the first drug remains in the catheter; and
transferring the second drug from the reservoir to the catheter in accordance with a second delivery profile, which is different than the first delivery profile, after the first drug has been cleared from the catheter in accordance with the first delivery profile and the at least one bolus delivery request.

21. A method as claimed in claim 20, wherein at least one of the first and second delivery profiles specifies a schedule of at least two different flow rates during portions of a period of certain duration.

22. A method as claimed in claim 20, further comprising the step of:
determining the quantity of the first drug remaining in the drug delivery device after the first drug as been evacuated from the reservoir by monitoring the activity of the fluid transfer device after the first drug has been evacuated from the reservoir.

23. A method as claimed in claim 21, wherein the period of certain duration comprises a twenty-four hour period.

24. A method as claimed in claim 22, wherein
the fluid transfer device comprises a pump; and
the step of monitoring the activity of the fluid transfer device after the first drug has been evacuated from the reservoir comprises monitoring pump strokes after the first drug has been evacuated from the reservoir.

* * * * *

UNITED STATES PATENT AND TRADEMARK OFFICE
CERTIFICATE OF CORRECTION

PATENT NO. : 7,347,854 B2  Page 1 of 1
APPLICATION NO. : 11/069573
DATED : March 25, 2008
INVENTOR(S) : Brian M. Shelton et al.

It is certified that error appears in the above-identified patent and that said Letters Patent is hereby corrected as shown below:

In Col. 8, line 18
replace "drug delivery"
with --drug delivery device.--

Signed and Sealed this

First Day of July, 2008

JON W. DUDAS
*Director of the United States Patent and Trademark Office*